US008461106B2

(12) United States Patent
Cohen et al.

(10) Patent No.: US 8,461,106 B2
(45) Date of Patent: Jun. 11, 2013

(54) BIOFILM PREVENTION USING LACTOFERRIN

(75) Inventors: Noam A Cohen, Bala Cynwyd, PA (US); Bert W. O'Malley, Jr., Villanova, PA (US); Alexander G. Chiu, Villanova, PA (US); James N. Palmer, Narberth, PA (US); Jacob D. Steiger, Highland Beach, FL (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 283 days.

(21) Appl. No.: 12/668,489

(22) PCT Filed: Jul. 9, 2008

(86) PCT No.: PCT/US2008/008415
§ 371 (c)(1), (2), (4) Date: Aug. 9, 2010

(87) PCT Pub. No.: WO2009/009065
PCT Pub. Date: Jan. 15, 2009

(65) Prior Publication Data
US 2010/0298208 A1 Nov. 25, 2010

Related U.S. Application Data

(60) Provisional application No. 60/929,674, filed on Jul. 9, 2007.

(51) Int. Cl.
*A61K 38/40* (2006.01)
(52) U.S. Cl.
USPC ........................................................ 514/2.5
(58) Field of Classification Search
None
See application file for complete search history.

(56) References Cited

U.S. PATENT DOCUMENTS

| | | |
|---|---|---|
| 2002/0119207 A1 | 8/2002 | Baker, Jr. et al. |
| 2005/0143286 A1* | 6/2005 | Singh et al. ................ 514/2 |
| 2006/0052452 A1 | 3/2006 | Scholz |
| 2007/0021342 A1 | 1/2007 | Breen et al. |
| 2007/0116750 A1 | 5/2007 | Wolcott |

OTHER PUBLICATIONS

Singh et al., "A component of innate immunity prevents bacterial biofilm development", Nature, 2002, 417:552-555.*
Hoffman et al., "Aminoglycoside antibiotics induce bacterial biofilm formation", Nature, Aug. 2005, vol. 436(25):1171-1175.*
Ramadan et al., "Chronic rhinosinusitis and biofilms", Otolaryngology—Head and Neck Surgery, Mar. 2005 , vol. 132, pp. 414-417.*
Dunne, W.M., "Bacterial Adhesion: Seen Any Good Biofilms Lately?", Clin Microbiol Rev. Apr. 2002; 15(2): 155-166.*
Chen et al., "Biofilm Removal Caused by Chemical Treatments", Wat. Res. vol. 34, No. 17, pp. 4229-4233, 2000.*
Simões et al., "Control of Flow-Generated Biofilms With Surfactants Evidence of Resistance and Recovery", Trans IChemE, Part C, Dec. 2006, Food and Bioproducts Processing, 84(C4): 338-345.*
Geesey, et al., Can. J. Microbiol. 32. 1733 6, 1977; 1994.
Boivin and Costerton, Elsevier Appl. Sci., London, 53 62, 1991.
Khoury, et al., ASAIO, 38, M174 178, 1992.
Costerton, et al., J. Bacteriol., 176, 2137 2142, 1994.
Powell, M. J. and Ogden, J. E., Nucleic Acids Res. 18:4013 (1990).
Moskowitz, S.M., J.M. Foster, J. Emerson, et al., Clinically Feasible Biofilm Susceptibility Assay for Isolates of *Pseudomonas aeruginosa* from Patients with Cystic Fibrosis. J Clin Microbiol, 2004. 42(5): p. 1915-22.

* cited by examiner

*Primary Examiner* — Suzanne M Noakes
(74) *Attorney, Agent, or Firm* — Mark S. Cohen; Pearl Cohen Zedek Latzer, LLP (57) ABSTRACT

This invention relates to methods and compositions capable of inhibiting biofilm formation. Specifically, provided herein are methods and compositions using Lactoferrin for the inhibition of biofilm formation.

40 Claims, 7 Drawing Sheets

BIOFILM PREVENTION USING LACTOFERRIN

CROSS-REFERENCE TO RELATED APPLICATIONS

This application is a National Phase Application of PCT International Application PCT/US2008/008415, filed Jun. 9, 2008, claiming priority to U.S. Provisional Patent Application 60/929,674, filed Jun. 9, 2007, which is incorporated by reference herein in its entirety.

FIELD OF INVENTION

This invention is directed to methods and compositions capable of inhibiting biofilm formation. Specifically, provided herein are methods and compositions using Lactoferrin for the inhibition of biofilm formation.

BACKGROUND OF THE INVENTION

Figure 1:
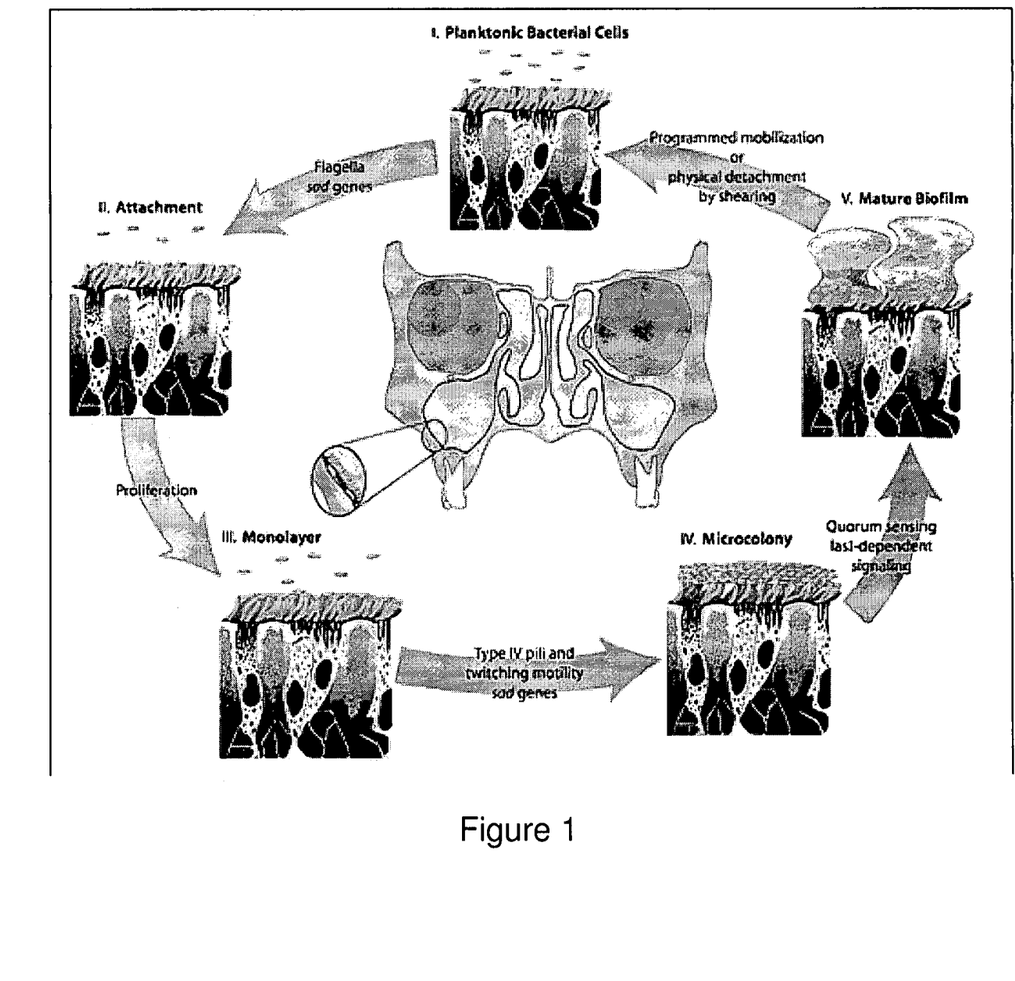
FIG. 1 shows the life cycle of biofilm.

Bacterial biofilms are a complex organization of bacteria anchored to a surface. They begin as a random collection of independent free-floating, planktonic bacteria, which then is attach to a surface and begin to form microcolonies. When bacterial density reaches a critical point, inter-bacterial crosstalk triggers a phenomenon known as "quorum sensing." Quorum sensing in turn initiates a cascade of protein expression which ultimately leads to the biofilm phenotype. This phenotype is marked by the formation of towers composed of layers of embedded live bacteria with intertwining water channels nourishing the individual bacteria and demonstrates a functional heterogeneous community. The "mortar" for these structures is comprised of a bacterially extruded exopolysaccharide matrix, which makes up as much as 90% of the biofilm. Importantly, the bacterial component of the biofilm can revert back to the mobile/planktonic state either through intrinsic (bacterial genetic program) or extrinsic (sheer stress) forces thereby causing new acute infections in remote sites (FIG. 1).

Existing in the biofilm phenotype, bacteria can evade host defenses and demonstrate massively decreased susceptibility to antibiotic therapy. For example, the minimal biofilm eradication concentration (MBEC) for *pseudomonas* biofilms has been demonstrated to be 60 fold greater than the MIC (for planktonic *pseudomonas*) for gentamicin and greater than 1,000 fold for ceftazidime and piperacillin. Thus, in the biomedical context, infections with associated biofilm formation are very problematic because of their increased resistance to antibiotic therapy and chronic cyclical persistence.

The typical clinical scenario of a biofilm associated infection, is clinical resolution of the initial presenting symptoms while the patient is undergoing antibiotic therapy, i.e, the planktonic bacteria are cleared. However, shortly after antibiotic therapy is terminated the patient presents with symptoms identical to the initial presentation since bacteria in the biofilm state survived therapy and reinfected the host with planktonic cells. Typically, the organisms cultured from the ensuing infections are identical in speciazation and sensitivities as the initial infection (demonstrating non plasmid associated resistance). Biofilms have now been implicated in many infectious processes, including dental caries, periodontitis, otitis media, musculoskeletal infections, necrotizing fasciitis, biliary tract infection, osteomyelitis, to bacterial prostatitis, native valve endocarditis, cystic fibrosis pneumonia as well as infections associated with all hardware (artificial joints, valves, shunts etc.). Recent studies have identified biofilms in the sinus mucosa of patients with chronic rhinosinusitis.

Therefore, there is a need for methods and compositions that are capable of inhibiting is the formation and growth of biofilms.

SUMMARY OF THE INVENTION

In one embodiment, the invention provides a method of inhibiting a bacterial biofilm formation, comprising the step of contacting the biofilm-forming bacteria with a composition comprising a recombinant Lactoferrin (rLF).

In another embodiment, the invention provides a method of inhibiting biofilm formation by a bacterium, comprising the step of contacting the bacterium with a composition comprising recombinant human Lactoferrin (rhLF).

In one embodiment, the invention provides a method of treating post-surgical chronic rhinosinusitis, comprising the step of contacting the affected area with a composition comprising a recombinant human Lactoferrin (rhLF), thereby preventing biofilm formation.

In another embodiment, provided herein is a method of treating Acute and Chronic rhinosinusitis, Serous Otitis Media, Acute and Chronic Otitis Media, Acute and Chronic Otitis Externa, Cystic Fibrosis pneumonia, Pneumonia, Bronchitis, Bronchiectasis, Acute exacerbation of chronic bronchitis, Acute and Chronic bronchitis, Chronic tonsillitis, Chronic pharyngitis, Oral cutaneous and pharyngocutaneous fistula, Decubitus ulcers, Diabetic ulcers, Periodontal disease, Asthma, Chronic Obstructive Pulmonary Disease (COPD), or their combination in a subject, comprising the step of administering to the subject a composition comprising recombinant Lactoferrine, thereby preventing formation of bacterial biofilm.

In one embodiment, provided herein is a composition for inhibiting bacterial biofilm formation, comprising a recombinant human Lactoferrin (rhLF).

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

This invention relates in one embodiment to methods and compositions capable of inhibiting biofilm formation. Specifically, provided herein are methods and compositions using Lactoferrin for the inhibition of biofilm formation.

In one embodiment, the term "biofilms" refers to biological films that develop and persist at interfaces in aqueous environments (Geesey, et al., Can. J. Microbiol. 32. 1733 6, 1977; 1994; Boivin and Costerton, Elsevier Appl. Sci., London, 53 62, 1991; Khoury, et al., ASAIO, 38, M174 178, 1992; Costerton, et al., J. Bacteriol., 176, 2137 2142, 1994), in another embodiment, along the inner walls of conduit material in industrial facilities, or in another embodiment in household plumbing systems, or in another embodiment on medical implants, or in another embodiment or as foci of chronic infections. These biological films are composed in one embodiment, of microorganisms embedded in an organic gelatinous structure composed of one or more matrix polymers, which are secreted by the resident microorganisms. Biofilms develop in one embodiment, into macroscopic structures several millimeters or centimeters in thickness and cover large surface areas in another embodiment. In another embodiment, the term "biofilm" refers to highly structured, surface-attached communities of cells encased within a self-produced extracellular polymeric matrix.

In one embodiment, biofilms play a role in restricting or entirely blocking flow in plumbing systems and often decrease the life of materials through corrosive action mediated by the embedded bacteria. In another embodiment, biofilms are capable of trapping nutrients and particulates that can contribute to their enhanced development and stability.

In one embodiment, an aminoglycoside response regulator expressed by gram negative bacteria, which detects subtherapeutic concentrations of antibiotics (aminoglycosides), induces a phenotypic switch from the planktonic to biofilm state. Thus, in one embodiment, inadequate or inappropriate antibiotic therapy induces biofilm formation thereby eliminating the best opportunity of eradication of an infection.

In another embodiment, in normal mucosal surfaces, innate immunity proteins found in respiratory secretions protect against biofilm formation despite persistent exposure to pathogenic bacteria. In another embodiment, Lactoferrin is an innate immunity glycoprotein found in high concentrations at mucosal surfaces. It is a component of airway secretions, tears and breastmilk, and is among the most abundant proteins present in surface secretions. In another embodiment, Lactoferrin is secreted by local neutrophils and in one embodiment, binds to the cell membranes of gram negative bacteria, causing microbial cell injury and death.

In another embodiment, lactoferrin kills clinical strains of *Staphylcoccus aureus* and mucoid *Pseudomonas aeruginosa* isolated from airways of subject with cystic fibrosis (CF). Accordingly and in another embodiment, the methods provided herein are effective in inhibiting or suppressing bacterial biofilm formation whereby the bacteria is *Pseudomonas aeruginosa*.

Accordingly and in one embodiment, provided herein is a method of inhibiting a bacterial biofilm formation, comprising the step of contacting the biofilm-forming bacteria with a composition comprising a recombinant Lactoferrin (rLF).

In another embodiment, at high concentrations, lactoferrin has the ability to sequester iron essential for microbial respiration, leading in another embodiment, to inhibition of microbial growth. In one embodiment, Lactoferrin binds lipopolysaccharide and enhances bacterial killing by antibiotics. In one embodiment, sub-inhibitory concentrations of iron unsaturated lactoferrin inhibit *pseudomonas* biofilm formation by altering bacterial movement in one embodiment, or preventing the organisms from forming cell clusters in another embodiment, or both in yet another embodiment.

In one embodiment, Recombinant human lactoferrin (rhLF) is produced in *Aspergillus niger*, a filamentous fungi. It is structurally identical to native human lactoferrin with regards to its 3-dimensional structure and molecular weight. In another embodiment, Lactoferrin is efficient in treating methicillin resistant staph aureus osteomyelitis.

In one embodiment, the term "human lactoferrin protein," "human lactoferrin," or simply "hLF protein" or "hLF" refers to a full-length human lactoferrin polypeptide, e.g., a polypeptide having an amino acid sequence substantially as described by Powell, M. J. and Ogden, J. E., Nucleic Acids Res. 18:4013 (1990), which is incorporated herein by reference. In another embodiment, the term "human lactoferrin protein" refers to hLF wherein the protein backbone is modified. In another embodiment, backbone modifications are acetylations. In another embodiment, backbone modifications is carboxylation. In another embodiment, backbone modifications is glycosylation modifications. In another embodiment, backbone modifications is other processing variants of hLF. In one embodiment, natural human lactoferrin is recombinantly encoded human lactoferrin, which is expressed in another embodiment, in a transgenic nonhuman animal, such as a bovine, where the glycosylation pattern may be distinct from glycosylation patterns of naturally-occurring human lactoferrin obtained from human milk.

In one embodiment, the biofilm-forming bacteria which biofilm formation is sought to be inhibited, is a *Pseudomonas aeruginosa*. In one embodiment, planktonic bacteria, which are metabolically active, are adsorbed onto a surface which has large amounts of nutrients available for the initial colonization process. In another embodiment, once adsorbed onto a surface, the initial colonizing cells undergo phenotypic changes that in another embodiment, alter their functional activities and metabolic paths. In one embodiment, at the time of adhesion, *Pseudomonas aeruginosa* (*P. aeruginosa*) upregulates algC, or in another embodiment, algD, or in another embodiment, algU or in another embodiment, other genes and their combination, which control the production of phosphomanomutase in one embodiment and other pathway enzymes in other embodiment, which are involved in alginate synthesis. In one embodiment, alginate is the exopolysaccharide that serves as the polysaccharide backbone for *P. aeruginosa*'s biofilm. In one embodiment, this phenotypic transformation causes as many as 30 percent of the intracellular proteins to be different between planktonic and sessile cells of the same species. In another embodiment, the term "alginate" refers to a secreted extracellular polysaccharide composed of the uronic acid β-D-mannuronate and its C-5 epimer α-L-guluronate, which, in certain embodiments, is partially O-acetylated at the second or third position(s) of the D-mannuronate residues.

Accordingly and in one embodiment, provided herein is a method of inhibiting *Pseudomonas aeruginosa* from forming bacterial biofilm, comprising the step of contacting the *Pseudomonas aeruginosa* in its planktonic state with a composition comprising a recombinant Lactoferrin (rLF), thereby altering bacterial movement and preventing the organisms from forming cell clusters.

In one embodiment, the bacterial biofilm which formation is sought to be inhibited using the compositions and methods provided herein, is agent-induced. In one embodiment, the initial stages of biofilm formation require flagellar motility and type IV pili-mediated twitching for surface attachment and microcolony aggregation. In another embodiment, as bacterial cells continue to attach and form microcolonies, cell-cell signaling referred to in one embodiment, as "quorum sensing", use a population-dependent cell-cell signal, in one embodiment, an acylated homo-Ser lactone molecule, to detect cell density. When the concentration of this autoinducer reaches a critical concentration, a transcriptional regulator is activated in one embodiment, which induces specific target genes.

In one embodiment, two separate quorum-sensing systems, exist in *P. aeruginosa*; the las and rhl systems, that are responsible in another embodiment, for the regulation of numerous genes. In one embodiment, contacting the bacteria with the compositions described herein, using the methods described herein, interferes with the quorum sensing system thereby inhibiting biofilm formation.

In one embodiment, sub-therapeutic level of compounds capable of stressing bacteria induce the formation of biofilm. In another embodiment, the methods and compositions provided herein, are effective in the suppression of biofilm formation, induced by sub-therapeutic concentration of antibiotics. In another embodiment, the agent inducing biofilm formation is a detergent. In one embodiment, aminoglycoside antibiotics at subinhibitory concentrations induce biofilm formation in *Pseudomonas aeruginosa* and *Escherichia coli*. The formation of biofilm in response to sub-lethal concentrations of antibiotic is evolved in one embodiment, as a result of microbial competition, since most antibiotics are made by the bacteria themselves.

For example, in one embodiment, *Staphylococcus epidermidis* causes polymer-associated infections and depends on the expression of the icaADBC operon leading to the synthesis of a polysaccharide intercellular adhesion for the formation of biofilm. In another embodiment, subinhibitory concentrations of tetracycline, erythromycin or the semisynthetic is streptogramin antibiotic quinupristin-dalfopristin enhance ica expression and biofilm formation. In one embodiment, the methods and compositions provided herein, inhibit or suppress antibiotic-induced film formation of *S. epidermidis*.

In another embodiment biofilm formation is induced by external stress such as high temperature in one embodiment, or osmolarity in another embodiment. In one embodiment, the environmental stress inducing biofilm formation is detergents or surfactants. In one embodiment, biofilms of *P. fluorescens* developed on silicone and stainless-steel surfaces treated with benzalkonium chloride (BC), a cationic surfactant, showing higher biomass and respiratory activity than the biofilms formed on the untreated surfaces. In another embodiment, the presence of bile, a natural detergent on catheters and stents, induces *E. faecalis* strains to form biofilm.

In one embodiment the inhibition or suppression of biofilm formation using the methods and compositions described herein, is effective against biofilm induced by cephalosporin antibiotic. In another embodiment, the antibiotic is aminoglycoside. In another embodiment, the antibiotic is cefdinir. In another embodiment, the antibiotic is ofloxacin. In another embodiment, the antibiotic is tobramycin.

In one embodiment, inhibiting, suppressing or preventing a bacterial biofilm formation, comprising the step of contacting the biofilm-forming bacteria with a composition comprising a recombinant Lactoferrin (rLF) whereby contacting the bacteria is done using topical irrigation with a composition comprising rLF.

In another embodiment, the bacterial biofilm is associated with chronic rhinosinusitis. The term "chronic rhinosinusitis" (CRS) or in another embodiment, "allergic fungal sinusitis" (AFS) refers to the presence of inspissated mucus in the nasal-paranasal cavities. In one embodiment, biofilms in the nasopharynx of subjects with CRS acts as a chronic reservoir for bacterial pathogens resistant to standard antibiotics, thereby exacerbating CRS. In another embodiment, biofilm formation by *Pseudomonas aeruginosa* and *Staphylococcus aureus* correlate with unfavorable evolution after endoscopic sinus surgery (ESS). In one embodiment, the methods described herein are effective in inhibition, suppression or prevention of biofilm associated with CRS or AFS. In another embodiment, the method described herein, are carried out following ESS. In another embodiment, the method described herein, are carried out following adenoidectomy.

In one embodiment, the methods provided herein, further comprise contacting the biofilm forming bacteria with an antibiotic agent. In another embodiment, contacting is via intramuscular administration. In another embodiment, contacting is via intraarticular administration. In another embodiment, contacting is via intranasal administration. In another embodiment, contacting is via transnasal administration. In another embodiment, contacting is via parenteral administration. In another embodiment, contacting is via oral administration. In another embodiment, contacting is via aerosolized administration. In another embodiment, contacting is via their combination administration. Accordingly and in one embodiment, provided herein is a method of inhibiting or suppressing the formation of biofilm in a subject by *Pseudomonas aeruginosa*, following endoscopic sinus surgery (ESS), comprising the step of contacting the subject via intranasal administration, with a therapeutically effective composition comprising rLF and azythromycin, thereby interfering with quorum sensing and reducing cell motility. In another embodiment, the compositions provided herein are administered as combination therapy with both azythromycin and aminoglycoside antibiotics.

A person skilled in the art would readily recognize that contacting the subject with rLF as described in the methods provided herein, may be done before or after the administration of other antibiotics, or in another embodiment, before or after surgery. The use of rLF may reduce in certain embodiment, the threshold for lethality of antibiotics, or in other embodiments, the ability of the bacteria to develop resistance to the antibiotic agent.

In one embodiment, the rLF used in the methods and compositions provided herein, is a recombinant human Lactoferrin. In one embodiment, the term "recombinant" or "recombinant nucleic acid" refers to a nucleic acid that has a sequence that is not naturally occurring or in other embodiments, has a sequence that is made by an artificial combination of two otherwise separated segments of sequence. This artificial combination is accomplished in one embodiment, by chemical synthesis or, in another embodiment, by the artificial manipulation of nucleic acids, such as by the manipulation of at least one nucleic acid by a restriction enzyme in one embodiment, or ligase, recombinase, and/or a polymerase in other embodiments. Once introduced into a host cell, a recombinant nucleic acid is replicated in one embodiment by the host cell. In another embodiment, the recombinant nucleic acid once replicated in the cell remains a recombinant nucleic acid for purposes of this invention. In another embodiment, the term "recombinant protein" or "rhLF" or "recombinant human lactoferrin" refers to a protein produced by a method employing a recombinant nucleic acid. In one embodiment, provided herein is a method of inhibiting biofilm formation by a bacterium, comprising the step of contacting the bacterium with a composition comprising recombinant human Lactoferrin (rhLF).

In another embodiment, provided herein is a method of treating post-surgical chronic rhinosinusitis, comprising the step of contacting the affected area with a composition comprising a recombinant human Lactoferrin (rhLF), thereby preventing biofilm formation. In one embodiment, the term "contacting" refers to bringing a subject in contact with the compositions provided herein. For example, in one embodiment, the compositions provided herein are suitable for oral administration, whereby bringing the subject in contact with the composition comprises ingesting the compositions. In another embodiment, the compositions provided herein are suitable for topical administration, whereby administering the composition using a patch in another embodiment brings the subject in contact with the compositions provided herein through topical irrigation. In one embodiment, the compositions provided herein are in an aerosolized form and are inhaled directly by the subject, thereby bringing the subject in contact with the compositions provided herein.

A person skilled in the art would readily recognize that the methods of bringing the subject in contact with the compositions provided herein, will depend on many variables such as, without any intention to limit the modes of administration; the age of the subject, pre-existing conditions, other agents administered to the subject, the severity of symptoms, location of the affected area and the like. In one embodiment, provided herein are embodiments of methods for administering the compounds of the present invention to a subject, through any appropriate route, as will be appreciated by one skilled in the art.

In another embodiment, provided herein is a method of treating Acute and Chronic rhinosinusitis, Serous Otitis Media, Acute and Chronic Otitis Media, Acute and Chronic Otitis Externa, Cystic Fibrosis pneumonia, Pneumonia, Bronchitis, Bronchiectasis, Acute exacerbation of chronic bronchitis, Acute and Chronic bronchitis, Chronic tonsillitis, Chronic pharyngitis, Oral cutaneous and pharyngocutaneous fistula, Decubitus ulcers, Diabetic ulcers, Periodontal disease, Asthma, Chronic Obstructive Pulmonary Disease (COPD), or their combination in a subject, comprising the step of administering to the subject a composition comprising recombinant Lactoferrine, thereby preventing formation of bacterial biofilm.

In one embodiment, bacterial biofilms form on the middle-ear mucosa of subjects having *H. influenzae* induced otitis media and in another embodiment form on tympanostomy tubes placed in children's ears. In another embodiment biofilms, resistant to treatment by antibiotics and to detection by standard culture techniques, play a major etiologic role in OME and in another embodiment, in one of its frequent complications, post-tympanostomy otorrhea. In one embodiment, the methods and compositions provided herein, are effective in suppressing or inhibiting biofilm formation by *Streptococcus pneumoniae*, or *Moraxella catarrhalis*, or both.

In another embodiment, "periodontal disease" refers to periodontal tissue destruction caused by the action of toxic products released in the sub-gingival area by specific periodontal pathogens. *Treponema denticola* is a small helically shaped obligate anaerobic spirochaete frequently isolated from the periodontal pocket and correlated with the severity of periodontal disease. In another embodiment, biofilms are important in the oral cavity where primary colonizers such as *T. denticola* in one embodiment, attach to oral surfaces thereby enhancing colonization by other bacteria which are themselves poor colonizers. Another major Gram-negative rod bacterium which has been associated with periodontitis is *Porphyromonas gingivalis*. In another embodiment, there is a symbiotic relationship between these two periodontopathogens for nutrients. In one embodiment, interaction between *T. denticola* and *P. gingivalis* in biofilm formation plays an important role in the initial stages of the onset of periodontal disease. In one embodiment, biofilm formed by *T. denticola* causes periodontal disease. In one embodiment, the compositions and methods provided herein are effective in preventing the formation of biofilm in the oral cavity, thereby preventing periodontal disease. Accordingly in one embodiment, the compositions provided herein are formulated as part of toothpaste's active ingredients.

In one embodiment, bacteria that adhere to solid surfaces, implanted medical devices or in another embodiment, to damaged tissue can become the focus of persistent infections, evading in another embodiment clearance by the host defenses and by antimicrobial chemotherapy by growing in biofilms in which they are protected. In one embodiment, the bacterial biofilm infections are formed by *Staphylococcus aureus* or in another embodiment, by *Staphylococcus epidermidis*. Biofilm infections that involve staphylococcal strains include in one embodiment, those associated with sutures. In another embodiment biofilm infections that involve staphylococcal strains include those associated with Hickman catheters. In another embodiment biofilm infections that involve staphylococcal strains include those associated with central venous catheters. In another embodiment biofilm infections that involve staphylococcal strains include those associated with prosthetic heart valves. In another embodiment biofilm infections that involve staphylococcal strains include those associated with vascular grafts, or in another embodiment biofilm infections that involve staphylococcal strains include those associated with a combination thereof.

Accordingly and in one embodiment, provided herein is a method of inhibiting biofilm formation by a bacterium on a solid surface, comprising the step of contacting the bacterium with a composition comprising recombinant human Lactoferrin (rhLF). In one embodiment, the solid surface upon which the biofilm inhibition is sought to be affected using the methods described herein and the compositions described herein is sutures, or in another embodiment, the solid surface is an implantable medical device or in another embodiment, the solid surface is a surgical table or tool and the like.

In one embodiment, subtherapeutic antibiotic levels will induce biofilm formation on solid surfaces, thereby reducing the susceptibility of the bacteria to any added levels of antibiotics. In one embodiment, the methods provided herein, comprising the step of contacting the bacterium with a composition comprising recombinant human Lactoferrin (rhLF), prevents the antibiotic-induced biofilm formation.

Catheter-related sepsis refers in one embodiment to a clinical syndrome characterized by the presence of a catheter-associated infection along with a systemic inflammatory response. In another embodiment, following CVC insertion, the intravascular portion of the device is covered rapidly by a thrombin layer, rich in host-derived proteins acting as a detergent, which forms a conditioning film and in another embodiment promotes surface adherence of microbial colonizers to form biofilms. These microorganisms enter a sessile mode of growth in one embodiment, secreting an exopolysaccharide slime within which organism density is regulated by quorum-sensing molecules. In another embodiment, these microorganisms are dispersed in clumps that in one embodiment become septic emboli. Antiadhesive, antiseptic, and antibiotic coatings of catheters have demonstrated only modest clinical efficacy. Accordingly, in one embodiment, coating CVC with the compositions provided herein, may be used to prevent detergent induced biofilm growth.

In another embodiment, the methods and compositions described herein are applicable to preventing or inhibiting a variety of bacterial infections of plants. Pseudomonadaceae, Rhizobiaceae, Enterobacteriaceae, Corynebacteriaceae and Streptomycetaceae bacteria are all economically significant plant pathogens that may be controlled by the present invention. In one embodiment, the plant pathogens that may be effectively inhibited using the methods and compositions described herein include: *Xanthomonas* species, such as, for example, *Xanthomonas campestris* pv. *oryzae*; *Pseudomonas* species, such as, for example, *Pseudomonas syringae* pv. *lachrymans*; and *Erwinia* species, such as, for example, *Erwinia amylovora*. It is also anticipated that the methods of preventing or inhibiting bacterial infections of plants described herein may also include use of compositions further comprised of antimicrobial agents such as bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Methods of preventing or inhibiting bacterial infections described herein can be used to treat all plants and parts of plants. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and the parts of plants with the active compounds as described herein, is carried out directly or by action on their surroundings, habitat or storage space, according to customary treatment methods, such as in one embodiment, by dipping, or spraying, evaporating, atomizing, broadcasting, spreading-on in other embodiments; and, in the case of propagation material, in particular in the case of seeds, furthermore by one- or multi-layer coating of the compositions comprising the rLF as described herein. In certain embodiments the active compound is a rLF. In another embodiment, the rLF is combined in the composition with another active compound that is an antimicrobial agent or antibiotic.

In another embodiment, the compositions described herein may also be used to prevent or reduce biofilm formation or microbial adhesion in marine and freshwater applications, or in aqueous handling (storage or transport) or treatment systems, by applying such a composition to surfaces of that are in, or are to be placed into, contact with an aqueous environment e.g. ships and marine vessels, docks, oil rigs and platforms, oceanic cabeling and piping, bridges. Such compositions can also be used as biofilm release enhancers, such as for use on re-usable components of such marine, freshwater, and aqueous handling or treatments systems, e.g., mesh screens, filter plates, filtering cartridges, and the like.

In another embodiment, baby shampoo/chemical surfactant at a 0.2-5% concentration is effective in inhibiting the formation of biofilms. In another embodiment, baby shampoo/chemical surfactant at a 0.2-1% concentration is effective in inhibiting the formation of biofilms. In another embodiment, baby shampoo/chemical surfactant at a 0.5-1.5% concentration is effective in inhibiting the formation of biofilms. In another embodiment, baby shampoo/chemical surfactant at a 0.8-2% concentration is effective in inhibiting the formation of biofilms. In another embodiment, baby shampoo/chemical surfactant at a 1-3% concentration is effective in inhibiting the formation of biofilms. In another embodiment, baby shampoo/chemical surfactant at a 2-5% concentration is effective in inhibiting the formation of biofilms.

In another embodiment, baby shampoo/chemical surfactant at a 0.2-5% concentration is effective in eradicating planktonic pseudomonas. In another embodiment, baby shampoo/chemical surfactant at a 0.2-1% concentration is effective in eradicating planktonic pseudomonas. In another embodiment, baby shampoo/chemical surfactant at a 0.5-1.5% concentration is effective in eradicating planktonic pseudomonas. In another embodiment, baby shampoo/chemical surfactant at a 0.8-2% concentration is effective in eradicating planktonic pseudomonas. In another embodiment, baby shampoo/chemical surfactant at a 1-3% concentration is effective in eradicating planktonic pseudomonas. In another embodiment, baby shampoo/chemical surfactant at a 2-5% concentration is effective in eradicating planktonic pseudomonas.

In another embodiment, baby shampoo/chemical surfactant at a 0.2-5% concentration is effective in inhibiting the formation of biofilms and eradicating planktonic pseudomonas in a difficult to treat patient population. In another embodiment, baby shampoo/chemical surfactant at a 0.2-5% concentration is effective in inhibiting the formation of biofilms and eradicating planktonic pseudomonas in a an asthmatic patients.

In another embodiment, baby shampoo/chemical surfactant at a 0.2-5% concentration is effective as an adjuvant therapy combined with other treatments known to one of skill in the art, in inhibiting the formation of biofilms and eradicating planktonic pseudomonas. In another embodiment, surfactants are effective as an adjuvant therapy combined with other treatments known to one of skill in the art, in inhibiting the formation of biofilms and eradicating planktonic pseudomonas. In another embodiment, anionic surfactants are effective as an adjuvant therapy combined with other treatments known to one of skill in the art, in inhibiting the formation of biofilms and eradicating planktonic *pseudomonas*.

In another embodiment, surfactants inhibit the formation of biofilms and eradicate planktonic *pseudomonas*. In another embodiment, anionic surfactants inhibit the formation of biofilms and eradicate planktonic pseudomonas. In another embodiment, surfactants at a 0.2-5% concentration are effective in inhibiting the formation of biofilms and eradication of planktonic pseudomonas. In another embodiment, anionic surfactants are effective in inhibiting the formation of biofilms and eradication of planktonic pseudomonas.

In another embodiment, baby shampoo/chemical surfactant at a 0.2-5% concentration is effective in improving SNOT-22 scores. In another embodiment, baby shampoo/chemical surfactant at a 0.2-5% concentration is effective as an adjuvant therapy combined with other treatments known to one of skill in the art in improving SNOT-22 scores. In another embodiment, surfactants are effective in improving SNOT-22 scores. In another embodiment, surfactants are effective as an adjuvant therapy combined with other treatments known to one of skill in the art, in improving SNOT-22 scores. In another embodiment, anionic surfactants are effective in improving SNOT-22 scores. In another embodiment, anionic surfactants are effective as an adjuvant therapy combined with other treatments known to one of skill in the art, in improving SNOT-22 scores.

In another embodiment, baby shampoo/chemical surfactant at a 0.2-5% concentration is effective in reducing thickened nasal secretions and/or post-nasal drainage. In another embodiment, baby shampoo/chemical surfactant at a 0.2-5% concentration is effective as an adjuvant therapy combined with other treatments known to one of skill in the art in reducing thickened nasal secretions and/or post-nasal drainage. In another embodiment, surfactants are effective reducing thickened nasal secretions and/or post-nasal drainage. In another embodiment, surfactants are effective as an adjuvant therapy combined with other treatments known to one of skill in the art, in reducing thickened nasal secretions and/or post-nasal drainage. In another embodiment, anionic surfactants are effective reducing thickened nasal secretions and/or post-nasal drainage. In another embodiment, anionic surfactants are effective as an adjuvant therapy combined with other treatments known to one of skill in the art, reducing thickened nasal secretions and/or post-nasal drainage.

In another embodiment, baby shampoo/chemical surfactant at a 0.2-5% concentration is effective as a sinus rinse for patients with biofilm chronic rhinosinusitis. In another embodiment, baby shampoo/chemical surfactant at a 0.2-5% concentration is effective as an adjuvant therapy combined with other treatments known to one of skill in the art as a sinus rinse for patients with biofilm chronic rhinosinusitis. In another embodiment, surfactants are effective as a sinus rinse for patients with biofilm chronic rhinosinusitis. In another embodiment, surfactants are effective as an adjuvant therapy combined with other treatments known to one of skill in the art, as a sinus rinse for patients with biofilm chronic rhinosinusitis. In another embodiment, anionic surfactants are effective as a sinus rinse for patients with biofilm chronic rhinosinusitis. In another embodiment, anionic surfactants are effective as an adjuvant therapy combined with other treatments known to one of skill in the art, as a sinus rinse for patients with biofilm chronic rhinosinusitis.

In another embodiment, provided herein a sinus rinse for patients with biofilm chronic rhinosinusitis, comprising baby shampoo/chemical surfactant at a 0.2-5% concentration. In another embodiment, provided herein a sinus rinse for patients with biofilm chronic rhinosinusitis, comprising baby shampoo/chemical surfactant at a 0.2-5% concentration combined with other treatments known to one of skill in the art. In another embodiment, surfactants are effective reducing thickened nasal secretions and/or post-nasal drainage. In another embodiment, provided herein a sinus rinse for patients with biofilm chronic rhinosinusitis, comprising surfactants. In another embodiment, provided herein a sinus rinse for patients with biofilm chronic rhinosinusitis, comprising anionic surfactants. In another embodiment, provided herein a sinus rinse for patients with biofilm chronic rhinosinusitis, comprising anionic surfactants combined with other treatments known to one of skill in the art.

Figure 7:
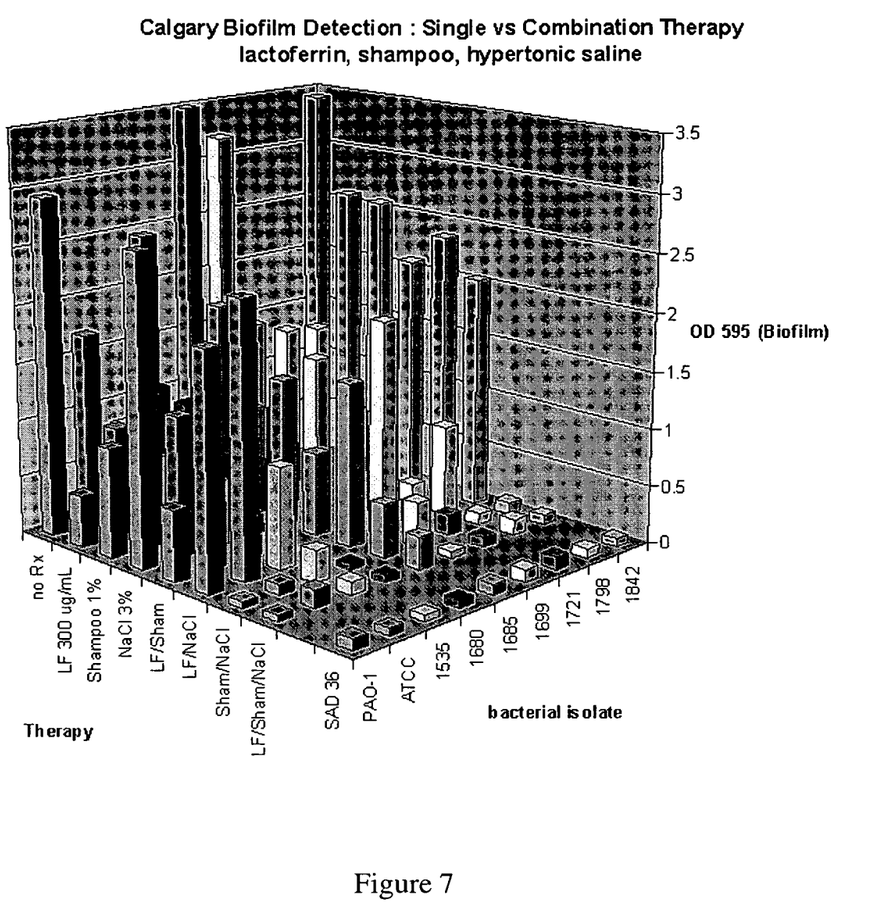
FIG. 7 show that a combination of lactoferrin, shampoo, and hypertonic saline results in complete biofilm inhibition in two commercially available strains of *pseudomonas* (PAO1, ATCC) as well as biofilm forming clinical isolates.

In another embodiment, provided herein that a combination comprising lactoferrin and shampoo/chemical surfactant is effective against biofilm formation of clinical isolates from patients with recalcitrant chronic rhinosinusitis (FIG. 7).

In one embodiment a novel sinus rinse for patients with biofilm chronic rhinosinusitis is provided. Although topical antibiotics are effective, they carry several risks including resistance, induction of the biofilm phenotype, and drug reactions as described hereinabove. In another embodiment, at a very narrow dose range of shampoo/chemical surfactant, biofilm formation is induced. In one embodiment, when lactoferrin is added to the shampoo/chemical surfactant, an inhibition of the moderate pseudomonal antibiofilm activity and induction is evident.

In one embodiment, the combination of lactoferrin and shampoo/chemical surfactant is effective against biofilm formation of clinical isolates from patients with recalcitrant chronic rhinosinusitis. As demonstrated in FIG. 7, the combination resulted in complete biofilm inhibition in two commercially available strains of pseudomonas (PAO1, ATCC) as well as 7 biofilm forming clinical isolates.

The term "subject" refers in one embodiment to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Materials and Methods

Biofilm growth is determined using the plate based assay described by Moskowitz et al [Moskowitz, S. M., J. M. Foster, J. Emerson, et al., Clinically Feasible Biofilm Susceptibility Assay for Isolates of *Pseudomonas Aeruginosa* from Patients with Cystic Fibrosis. J Clin Microbiol, 2004. 42(5): p. 1915-22]. *Pseudomonas aeruginosa* (PAO1) cultures are grown to log phase ($OD_{600}$=0.5) and 100 µl of culture is mixed with 25 µl of test 5× test substance and placed in 96 well flat bottom plates (Nalgene Nunc International, Rochester, N.Y.). A lid containing 96 polystyrene pegs (Nunc, TSP 96 well micro titer plate lid) is placed on top and the pegs are suspended in the wells. The lid is loosely fixed to the plate using a strip of parafilm (Menasha, Wis.). The plate is incubated without shaking at 37° C. for 20 hours at which time the lid containing the pegs is carefully removed from the 96 well culture plate and rinsed 3 times in sterile water. The pegs are placed in another 96 well plate containing Gram Crystal Violet (CV) (20 g/L CV, 8 g/L Ammonium Oxalate, 2% ethanol) for 15 min and then rinsed in sterile water three times to remove unbound crystal violet. The pegs are then immersed in a 96 well plate containing 200 ul of 100% EtOH for 15 minutes. The lid containing the pegs is removed from the eluted crystal violet and is read at 595 nm using a plate reader (Microplate Reader 680, Bio-Rad Hercules, Calif.).

Figure 2:
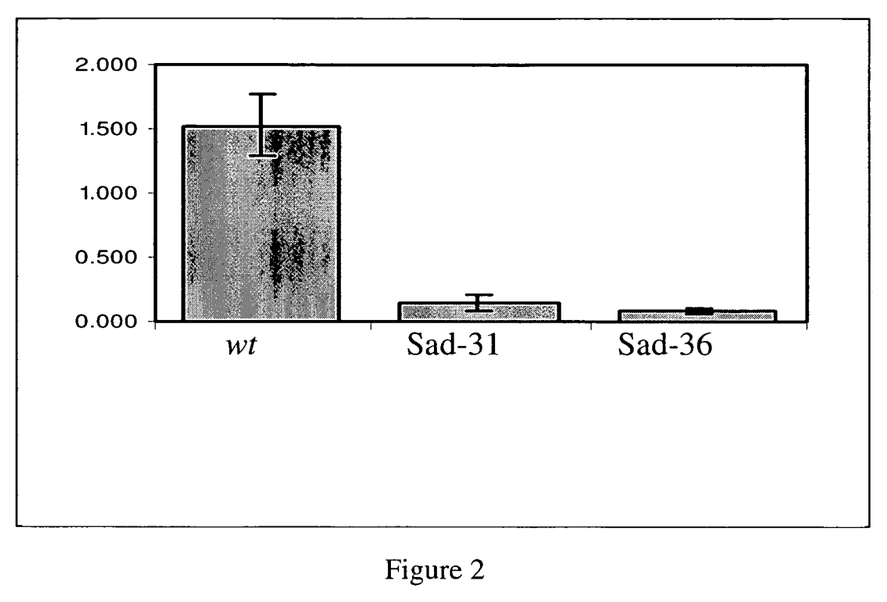
FIG. 2 shows biofilm detection using inverted polystyrene pegs. After 20 hours of growth wild type pseudomonas demonstrates robust biofilm formation compared to the Sad-31 and Sad-36 mutant strains. Absorbance at 595 nm is represented on the y-axis.

To demonstrate the ability of this assay to detect biofilms, rather than dead or clumped bacteria, two non-biofilm forming pseudomonal mutants (FIG. 2) were used. Sad-36 possesses a mutation in the flagella gene making it unable to transition from the planktonic to the adherent phenotype (FIG. 1, top left) while the sad-31 possesses a mutation in the type IV pili gene allowing it to adhere to the surface, but unable to organize into microcolonies (FIG. 1, bottom) (both mutants obtained through a generous gift from Dr. George O'Toole, Dartmouth University). These mutants are used as negative controls in each of the experiments to determine background signal above the blank.

Example 1

Lactoferrin Blocks the Antibiotic Induced Biofilm Formation

Figure 3:
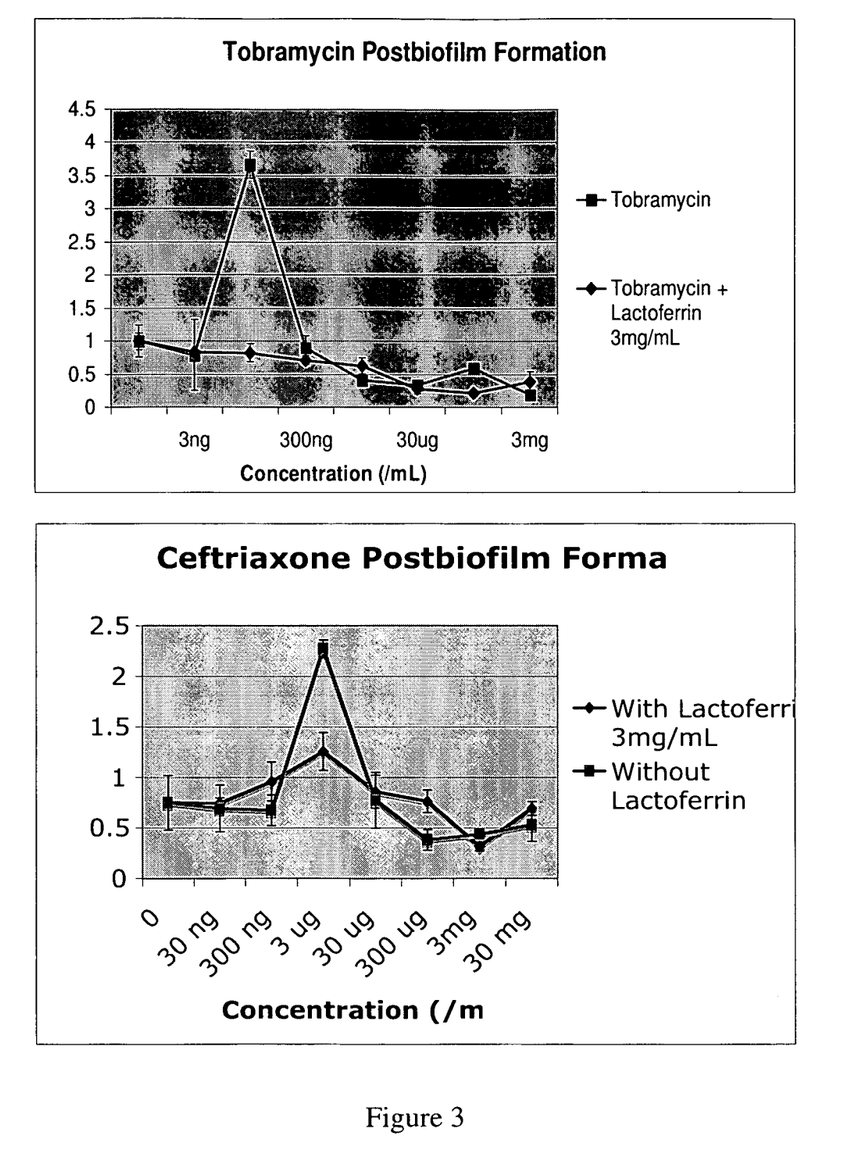
FIG. 3 shows induction of biofilm formation by subtherapeutic concentrations of Cephalosporins as well as aminoglycosides is blunted by the addition of rhLactoferrin.

In efforts to develop rationale topical therapy for post surgical chronic rhinosinusitis, a topical irrigation animal model of biofilm sinusitis was developed. The animal model was coupled to an in vitro biofilm eradication assay [Moskowitz, S. M., J. M. Foster, J. Emerson, et al., Clinically Feasible Biofilm Susceptibility Assay for Isolates of Pseudomonas Aeruginosa from Patients with Cystic Fibrosis. J Clin Microbiol, 2004. 42(5): p. 1915-22] for high throughput screening of combinations of therapies. During these efforts of combining rhLF with antibiotics the following observations were made: (a) antibiotic in other classes (cephalosporins) induce biofilm formation; and (b) the addition of lactoferrin blunts the antibiotic induced biofilm formation. As shown in FIG. 3 induction of biofilm formation by subtherapeutic concentrations of Cephalosporins as well as aminoglycosides is blunted by the addition of rhLactoferrin. Thus, rhLactoferrin is effective inhibits biofilm formation and development.

Example 2

Surfactants Induce Biofilm Formation

Figure 4:
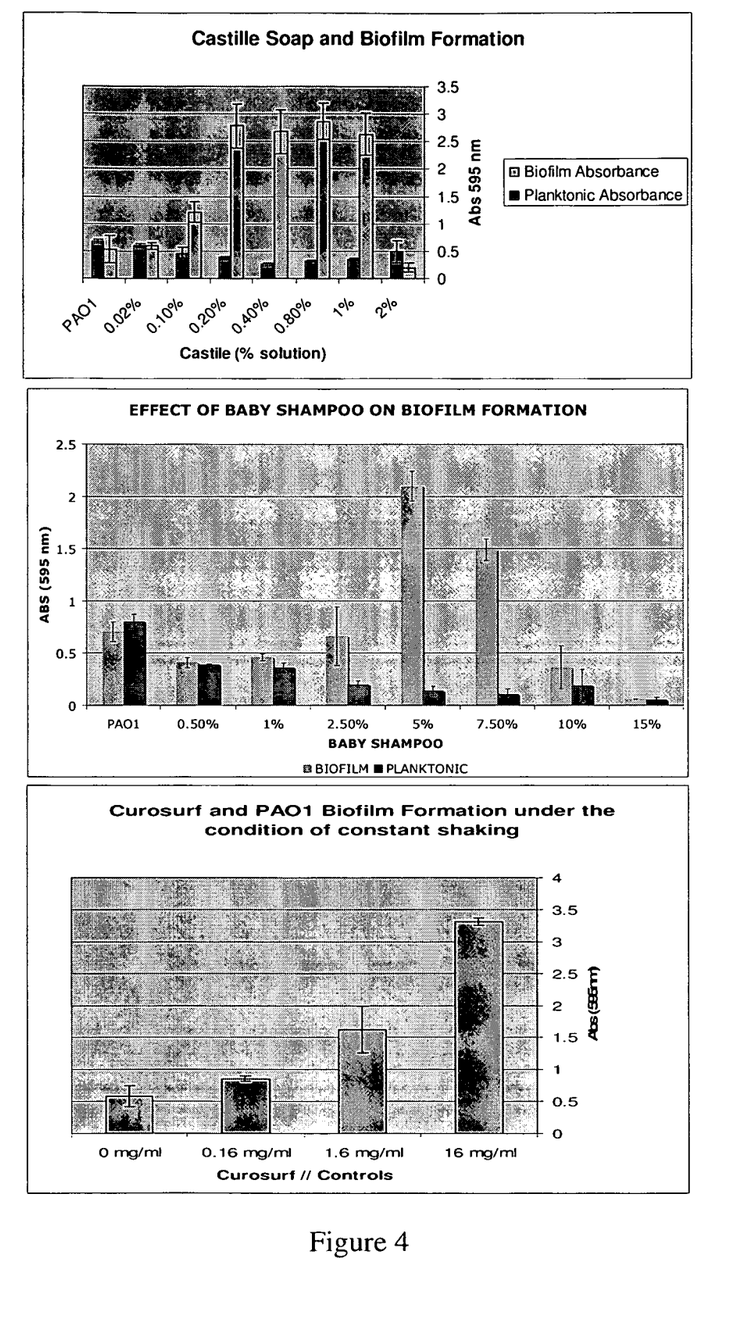
FIG. 4 shows the effects of commercially available detergents and therapeutic surfactant (Curosurf™) on pseudomonal biofilm formation. PAO-1 was incubated in increasing concentration of castile soap (top panel), Johnson and Johnson Baby Shampoo (middle panel) and Curosurf (bottom panel). Detergents had the expected result on planktonic bacteria (maroon bars) but demonstrated a biphasic (castile and baby shampoo) dose dependent induction of biofilms (blue bars)
Figure 5:
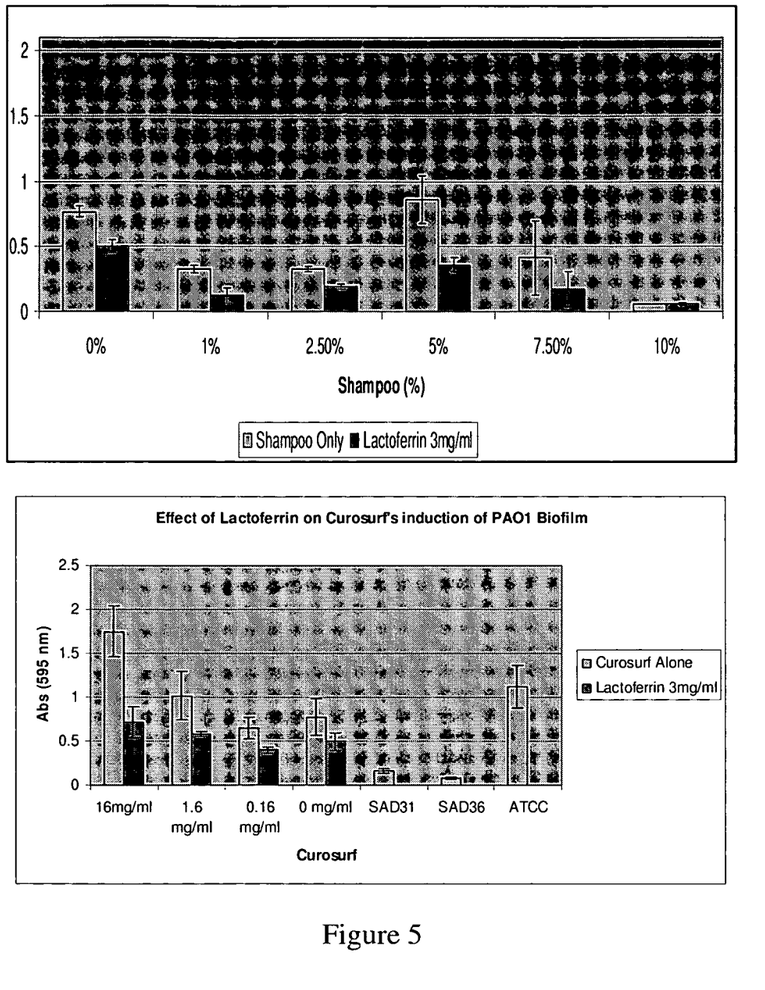
FIG. 5 show that rhLactoferrin inhibits detergent induced biofilm formation. Concomitant incubation with 3 mg/ml of rhLactoferrin blunts the induction of biofilm formation by Johnson and Johnson Baby Shampoo (top panel) as well as Curosurf (bottom panel).

Utilizing the same rationale and process described above, the utility of detergents and clinically used surfactants (biologic detergents) as a potential therapy for biofilm infection was investigated. Surprisingly, it was found that under certain conditions detergents can induce biofilm formation (FIGS. 4 and 5) and that rhLactoferrin inhibits detergent induced biofilm formation.

Example 3

Baby Shampoo/Chemical Surfactant Nasal Irrigations for the Symptomatic Post-Fess Patient A non-randomized study of CRS patients who remain symptomatic despite a previous history of sinus surgery and conventional medical therapy, including oral and topical steroids, antibiotics, oral and topical anti-histamines and saline irrigations was performed. Many of these patients had also received previous trials of "non-conventional" therapies, including topical antibiotic irrigations, systemic and topical anti-fungals and nebulized antibiotics.

Symptoms prior to and following treatment with baby shampoo/chemical surfactant irrigations were recorded using a validated quality of life form, the SNOT-224.

Objective assessment of olfactory function using the UPSIT5 was performed prior to and following therapy. Side effects and reasons for discontinuation were recorded in a patient diary, and the patients were seen four weeks after starting the baby shampoo/chemical surfactant irrigations.

The concentration of baby shampoo/chemical surfactant used for the clinical study was determined through in-vitro testing on planktonic pseudomonas aeruginosa and pre-formed pseudomonas aeruginosa biofilms. Bacterial and biofilm growth inhibition was determined using the plate based assay described in Moskowitz et al., (Clinically feasible biofilm susceptibility assay for isolates of Pseudomonas aeruginosa from patients with cystic fibrosis. J. Clinical Microbiology 2004; 42:1915-22). Briefly, PAO1 Pseudomonas aeruginosa bacterial strains were grown overnight. The following morning the culture was diluted to an $OD_{600}=0.1$ with Luria-Bertani broth (LB) and the sample again diluted 1:100 in LB. For determination of biofilm formation inhibition and growth inhibition 100 µl of diluted bacteria was added to 25 µl of a 5× concentrations of Johnson's Baby Shampoo/chemical surfactant (diluted in LB), placed in 96 well flat bottom plates (catalog number 269787, Nalgene Nunc International, Rochester N.Y.) in quadruplicate. A negative control of 25 µl of PBS added to 100 µl of medium was used, and showed no effect on biofilm formation or inhibition. A modified polystyrene microtiter lid with 96 pegs (catalog number 445497; Nunc TSP system) was placed into the bacterial isolate growth plate. The covered 96 well plates were incubated for 20 hours at 37° C. At the completion of the incubation the lid containing the pegs was removed and processed for biofilm detection while the 96 well plate was analyzed for bacterial growth by determination of absorbance at 600 nm. After incubation, the peg lid was rinsed three times in sterile water and the lid was placed in 2% crystal violet solution (Remel Inc, Lenexa Kans.) for 30 minutes to stain the biofilms adherent to the pegs. The peg lid was then rinsed again three times in sterile water, and dried for one hour. Next, the peg lid was inserted into a 96-well microtiter plate containing a 100% ethanol solution for 15 minutes. The peg lid was then discarded and the eluted crystal violate was read on a microtiter plate reader (Microplate Reader 680, Bio-Rad Hercules, Calif.) at an optical density of 595 nm (OD595). For determination of biofilm eradication, biofilms were generated on the peg as described above with the exception of omitting addition of the shampoo/chemical surfactant. Twenty hours later the lid was washed three times in sterile water and immersed in a 96 well plate contained pre diluted baby shampoo/chemical surfactant in LB. Quantification of residual biofilms was performed as described above.

Once the optimal concentration of baby shampoo/chemical surfactant was determined, patients were instructed to mix the solution in normal saline and irrigate with 60 cc on each side, twice a day for four weeks.

Figure 6:
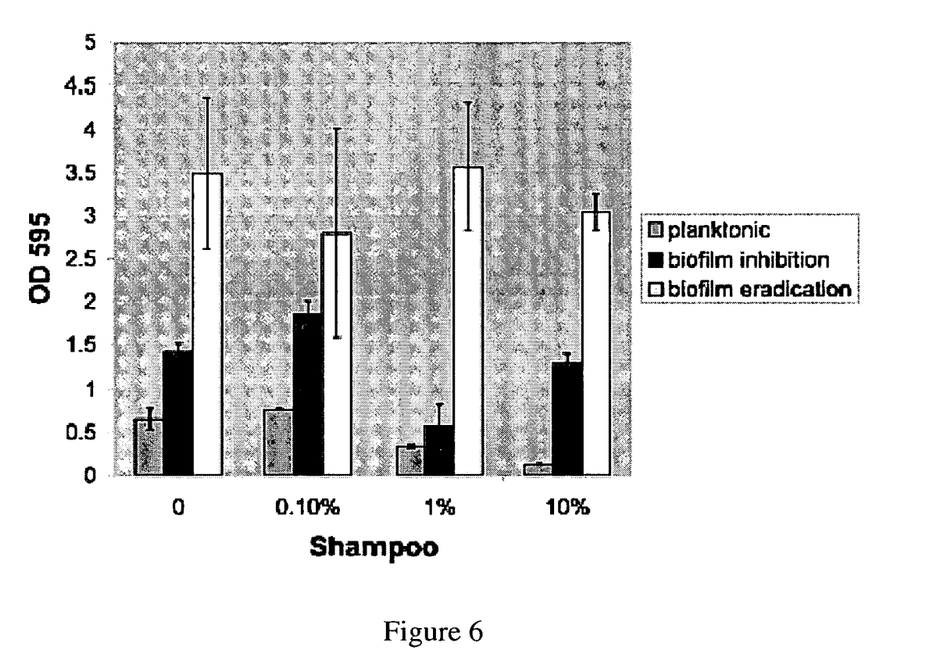
FIG. 6 show bacterial growth of *pseudomonas* (PAO1) treated with normal saline, 0.1%, 1% and 10% baby shampoo in normal saline. None of the solutions were able to eradicate pre-formed biofilms. 1 and 10% solutions eradicated planktonic bacteria ($p<0.05$) and the 1% solution was effective in inhibiting biofilm formation ($p<0.05$).

In-vitro testing showed that baby shampoo/chemical surfactant was unable to eradicate pre-formed pseudomonas biofilms at any concentration but at 1 and 10% is concentration, was effective in eradicating planktonic pseudomonas ($p<0.05$). Testing also showed that baby shampoo/chemical surfactant at 1% diluted in normal saline, significantly ($p<0.05$) inhibited the formation of biofilms compared to normal saline (FIG. 6). At 10% concentration, there was an increase in biofilm formation thus making 1% solution the determined concentration used for the clinical study.

Eighteen patients with CRS were prospectively followed as they irrigated with baby shampoo/chemical surfactant for 4 weeks. The average number of prior surgeries was 2.8 (range 1-6). Fifteen patients (83%) were asthmatics and each patient (100%) was using a topical nasal steroid spray and normal saline nasal irrigation prior to study initiation.

Three patients were excluded from final study analysis. One was lost to follow-up and two of the eighteen (11%) withdrew from the study, one from nasal irritation from the shampoo/chemical surfactant and the second after complaining of hives that eventually resolved with the discontinuation of the irrigation.

Fifteen patients completed a 4 week course of baby shampoo/chemical surfactant irrigations. Each patient continued their use of topical nasal steroid sprays during the study. Ten patients also received a concomitant 2 week course of antibiotics, and two patients were on a course of oral prednisone at the time of study. The average pre-treatment SNOT-22 score was 31.6 (Range 6-73). Overall subjective improvement after treatment was seen in 7 or 46.6% patients with an average decrease of 11.1 in their SNOT-22. None of the 7 patients who improved on shampoo/chemical surfactant irrigation received a concomitant course of oral prednisone, whereas 4 of the 7 had received a course of antibiotics along with their baby shampoo/chemical surfactant irrigation.

Looking at specific sub-divisions within the SNOT-22, the areas of greatest improvement were seen in response to post-nasal drainage and thickened mucus. Of the 15 patients in the study, 9 or 60% reported an improvement in the thickness of their discharge and 8 or 53.3% reported a decrease in post-nasal drainage.

Objective pre and post treatment smell testing was performed in 11 of the patients who completed the study. Seven of the 11 (63.6%) had an improvement in their UPSIT scores.

Thus, Baby shampoo/chemical surfactant containings the surfactant agents PEG-80 sorbitan laurate, Cocamidopropyl Betaine and Sodium Trideceth Sulfate that can act as a detergent to decrease the viscosity and surface tension of airway mucus.

Shampoo/chemical surfactant surfactants reduce the surface tension between water and grease, thereby causing the grease to be suspended in the water phase and preventing adsorption into the hair. This is achieved by the binding of grease at the center of a micelle structure with the hydrophilic portion of the surfactant pointing outward. These micelles are then washed away from the surface of the hair, resulting in the intended cleansing effect. The cleansing ability of a shampoo/chemical surfactant is dependent on the type and amount of surfactants used. Surfactants are classified according to hydrophilic polar group as anionic, cationic, zwitterionic and nonionic. In most products, a shampoo/chemical surfactant base consists of anionic and zwitterionic surfactants, such as the Cocamidopropyl Betaine (zwitterionic) and Sodium Trideceth Sulfate (anionic) found in Johnson's baby shampoo/chemical surfactant. These agents are effective cleansers and non-caustic to skin and mucus membranes. Cationic agents are often used in conditioners for their anti-static properties, but are poor cleansers and do not lather well. They are also strong irritants, and thus only used with less irritating surfactants in shampoo/chemical surfactants designed for dry hair.

In vitro testing showed that baby shampoo/chemical surfactant was unable to eradicate pre-formed pseudomonas biofilms. This may be due to the mild nature of the surfactants within the baby shampoo/chemical surfactant that are unable to break the bonds of the glycocalyx surrounding the biofilms. Cationic surfactants are the most toxic and have been used as antimicrobials, while anionics are less toxic and more active against gram positives than Gram-negatives. Since baby shampoo/chemical surfactant is largely made up of anionic and zwitterionic surfactants, their biocidal effects on the Gram-negative pseudomonas may be limited.

Although largely ineffective against pre-formed biofilms in this study, baby shampoo/chemical surfactant at a 1% concentration was effective in inhibiting the formation of biofilms in vitro as well as eradicating planktonic pseudomonas.

In a difficult to treat patient population, in which over 80% of patients were asthmatic and the average number of surgeries was nearly 3, adjuvant baby shampoo/chemical surfactant nasal irrigations provided subjective overall improvement in symptoms to nearly 50% of the patients studied, with the greatest benefit to those patients with chief complaints to of thick mucus discharge and post-nasal drainage.

Although the biocide capability of baby shampoo/chemical surfactant was not demonstrated in the in vitro trials, the use of surfactant as a nasal wash was supported in its moderate amount of success in an extremely difficult to treat patient population.

One percent baby shampoo/chemical surfactant nasal irrigations led to improvement in SNOT-22 scores for nearly 50% of patients that remained symptomatic despite surgical and conventional medical management. Greatest improvements were in symptoms of thickened nasal secretions and post-nasal drainage. Chemical surfactants within baby shampoo/chemical surfactant have a preventative role against bacterial biofilm formation via biocidal and/or mucolytic mechanisms of action. Further research is warranted into the clinical application of this novel, well-tolerated therapy.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of inhibiting a bacterial biofilm formation, comprising the step of contacting the biofilm-forming bacteria with a composition comprising a recombinant Lactoferrin (rLF) and a plurality of chemical surfactants comprising at least one zwitterionic surfactant and at least one anionic surfactant.

2. The method of claim 1, wherein the biofilm-forming bacteria is a *Pseudomonas aeruginosa.*

3. The method of claim 1, wherein the bacterial biofilm formation is agent-induced.

4. The method of claim 3, wherein the agent is an antibiotic, a detergent, or a surfactant.

5. The method of claim 4, wherein the antibiotic is a cephalosporin, an aminoglycoside, or their combination.

6. The method of claim 1, wherein the step of contacting comprises topical irrigation.

7. The method of claim 1, wherein the bacterial biofilm is associated with a chronic rhinosinusitis in a subject.

8. The method of claim 1, further comprising the step of contacting the biofilm-forming bacteria with an antibiotic compound.

9. The method of claim 1, wherein said Lactoferrin is human Lactoferrin (rhLF).

10. The method of claim 7, wherein said method is performed following chronic rhinosinusitis surgery in said subject.

11. A method of treating chronic rhinosinusitis in a subject, the method comprising the step of contacting an affected area in said subject with a composition comprising a recombinant human Lactoferrin (rhLF) and a plurality of chemical surfactants comprising at least one zwitterionic surfactant and at least one anionic surfactant, wherein said contacting prevents biofilm formation in said affected area, thereby treating said chronic rhinosinusitis in said subject.

12. The method of claim 11, wherein the step of contacting comprises topical irrigation.

13. The method of claim 11, wherein the chronic rhinosinusitis, is post-surgical chronic rhinosinusitis.

14. The method of claim 11, wherein the composition further comprises an antibiotic compound.

15. The method of claim 14, wherein the antibiotic compound is a cephalosporin, an aminoglycoside, or their combination.

16. A method of inhibiting biofilm formation by a bacterium on a solid surface, comprising the step of contacting the bacterium with a composition comprising recombinant human Lactoferrin (rhLF) and a plurality of chemical surfactants comprising at least one zwitterionic surfactant and at least one anionic surfactant.

17. The method of claim 16, whereby the solid surface is sutures, a surgical surface or body surface, surgical tools, or an implanted medical device.

18. The method of claim 16, whereby the surface is a component of fresh or saltwater ships or vessels, docks, bridges, pipes cabling, or all structures in contact with water or bodies of water.

19. The method of claim 16, whereby the surface is an agricultural product or component.

20. The method of claim 16, wherein the biofilm-forming bacteria is a *Pseudomonas aeruginosa*.

21. The method of claim 16, wherein the bacterial biofilm formation is agent-induced.

22. The method of claim 21, wherein the agent is an antibiotic, a detergent, or a surfactant.

23. The method of claim 22, wherein the antibiotic is a cephalosporin, an aminoglycoside, or their combination.

24. The method of claim 1, wherein said plurality of chemical surfactants are from a baby shampoo.

25. The method of claim 1, wherein said zwitterionic chemical surfactant is cocamidopropyl betaine.

26. The method of claim 1, wherein said anionic chemical surfactant is sodium trideceth sulfate.

27. The method of claim 1, wherein the chemical surfactants are used at a 0.2-5% concentration.

28. The method of claim 1, wherein the chemical surfactants are used at a 1% concentration.

29. The method of claim 11, wherein said plurality of chemical surfactants are from a baby shampoo.

30. The method of claim 11, wherein said zwitterionic chemical surfactant is cocamidopropyl betaine.

31. The method of claim 11, wherein said anionic chemical surfactant is sodium trideceth sulfate.

32. The method of claim 11, wherein the chemical surfactants are used at a 0.2-5% concentration.

33. The method of claim 32, wherein the chemical surfactants are at a 1% concentration.

34. The method of claim 16, wherein said plurality of chemical surfactants are from a baby shampoo.

35. The method of claim 16, wherein said zwitterionic chemical surfactant is cocamidopropyl betaine.

36. The method of claim 16, wherein said anionic chemical surfactant is sodium trideceth sulfate.

37. The method of claim 16, wherein the chemical surfactants are used at a 0.2-5% concentration.

38. The method of claim 37, wherein the chemical surfactants are used at a 1% concentration.

39. The method of claim 8, wherein the antibiotic compound is a cephalosporin, an aminoglycoside, or their combination.

40. The method of claim 11, wherein the chronic rhinosinusitis is recalcitrant chronic rhinosinusitis.

* * * * *